(12) United States Patent
Rice et al.

(10) Patent No.: US 9,995,757 B2
(45) Date of Patent: Jun. 12, 2018

(54) POINT OF CARE SICKLE CELL TEST

(71) Applicant: University of Florida Research Foundation, Inc., Gainesville, FL (US)

(72) Inventors: Mark J. Rice, Jacksonville, FL (US); Lindsay Bazydlo, Gainesville, FL (US); Timothy E. Morey, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days. days.

(21) Appl. No.: 14/917,741

(22) PCT Filed: Sep. 9, 2014

(86) PCT No.: PCT/US2014/054859
§ 371 (c)(1),
(2) Date: Mar. 9, 2016

(87) PCT Pub. No.: WO2015/035420
PCT Pub. Date: Mar. 12, 2015

(65) Prior Publication Data
US 2016/0216280 A1  Jul. 28, 2016

Related U.S. Application Data

(60) Provisional application No. 61/875,148, filed on Sep. 9, 2013.

(51) Int. Cl.
*G01N 33/72* (2006.01)
*G01N 33/49* (2006.01)
*G01N 21/31* (2006.01)
*G01N 21/35* (2014.01)

(52) U.S. Cl.
CPC ........... *G01N 33/721* (2013.01); *G01N 21/31* (2013.01); *G01N 21/35* (2013.01); *G01N 33/491* (2013.01); *G01N 33/726* (2013.01); *G01N 2201/12* (2013.01); *G01N 2333/805* (2013.01); *G01N 2800/22* (2013.01)

(58) Field of Classification Search
None
See application file for complete search history.

(56) References Cited

U.S. PATENT DOCUMENTS

| | | | |
|---|---|---|---|
| 4,088,448 A | 5/1978 | Lilja et al. | |
| 5,064,282 A | 11/1991 | Curtis | |
| 5,674,457 A | 10/1997 | Williamsson et al. | |
| 2009/0075324 A1 | 3/2009 | Pettersson | |
| 2012/0077218 A1* | 3/2012 | Randolph | G01N 33/52 435/29 |

FOREIGN PATENT DOCUMENTS

| | | |
|---|---|---|
| RU | 2316007 C2 | 1/2008 |
| WO | WO 2003/056327 A1 | 7/2003 |

OTHER PUBLICATIONS

International Search Report and Written Opinion dated Jan. 29, 2015 for PCT/US2014/054859.
International Preliminary Report on Patentability dated Mar. 24, 2016 for PCT/US2014/054859.
Hirsch et al., The relationship between the erythrocyte concentration and the specific electro conductivity of blood. Bull N Y Acad Med. Jun. 1948;24(6):393-4.
McMahon et al., A comparison of conductivity-based hematocrit determinations with conventional laboratory methods in autologous blood transfusions. Anesth Analg. Nov. 1990;71(5):541-4.
Luger et al., [Determination of hemoglobin concentration using the hemoglobin azide method in traumatic emergencies]. Anaesthesist. Feb. 1990;39(2):125-9. German. Erratum in: Anaesthesist Jun. 1990;39(6):340.
Vanzetti, An azide-methemoglobin method for hemoglobin determination in blood. J Lab Clin Med. Jan. 1966;67(1):116-26.

\* cited by examiner

*Primary Examiner* — Michelle F. Paguio Frising
(74) *Attorney, Agent, or Firm* — Wolf, Greenfield & Sacks, P.C.

(57) ABSTRACT

The disclosure provides methods, kits, and devices for determining an amount of hemoglobin S and/or an amount of total hemoglobin, and optionally, expressing the amount of hemoglobin S as a percentage. Devices of the disclosure may be used as point-of-care diagnostic systems accessible for use to a layperson, i.e., an individual with minimal or no medical training or expertise.

6 Claims, 1 Drawing Sheet

POINT OF CARE SICKLE CELL TEST

RELATED APPLICATIONS

This application is a National Stage Application of PCT/US2014/054859, filed on Sep. 9, 2014, which claims the benefit under 35 U.S.C. § 119(e) of U.S. provisional patent application, U.S. Ser. No. 61/875,148, filed Sep. 9, 2013, the entire content of each of which is incorporated by reference herein.

FIELD OF THE INVENTION

The invention, at least in part, relates to the field of molecular biology and medical devices for determining an amount of hemoglobin S and/or an amount of total hemoglobin, and, optionally, expressing the amount of hemoglobin S as a percentage in point-of-care methods, kits and related devices.

BACKGROUND

Sickle cell (SC) disease is a heritable hematological disorder characterized by the presence of hemoglobin S (Hb-S) that has a markedly decreased solubility in a deoxygenated state when compared to that of, for example, hemoglobin A.

Hb-S exists in a homozygous state (S/S) known as sickle cell anemia or in a heterozygous state (A/S) known as sickle cell trait. Homozygous (S/S) individuals commonly exhibit symptoms of severe hemolytic anemia and/or vascular occlusion, which can lead to complications including chronic fatigue; chronic pain; infections; lung, liver and heart injury; leg ulcers; retinopathies; inflammation; arthritis; splenomegaly; and chronic lung infections. While heterozygous (A/S) individuals are normally asymptomatic, they may also develop severe complications, including early end stage renal failure, renal medullary carcinoma, and polycystic kidney diseases.

Sickle Cell disease affects millions of people worldwide, however, Sickle Cell disease is most common in people whose ancestors came from Africa, South or Central America (especially Panama), Caribbean islands, Mediterranean countries (such as Turkey, Greece, and Italy), India, and Saudi Arabia. One-third of all indigenous inhabitants of Sub-Saharan Africa carry the Hb-S gene. In the United States, according to the Center for Disease Control and Prevention, about 90,000 to 100,000 people suffer from sickle cell anemia, while about 2 million Americans have sickle cell trait. Specifically, sickle cell anemia occurs among about 1 out of every 500 African Americans, while sickle cell trait occurs among about 1 out of every 12 African Americans.

Early diagnosis of sickle cell disease is essential for the prevention of Sickle Cell disease complications (such as infections) and for providing life-saving treatment. There is also a need for distinguishing sickle cell anemia from sickle cell trait.

In many circumstances, effective treatment of Sickle Cell disease and its corresponding complications requires rapid diagnosis often outside of the context of a medical facility or hospital. Thus, at the point-of-care, the diagnostic method would be most effective if it could be effectively used and a treatment decision reached by a layperson (i.e., an individual with minimal or no formal medical training or experience). Existing sickle cell screening tests include hemoglobin electrophoresis, genetic testing, high performance liquid chromatography (HPLC), isoelectric focusing, antibody-based assay, and mass spectrometry, all of which are time-consuming and are performed by highly trained health-care professionals in a laboratory setting.

SICKLEDEX™ is a qualitative solubility test used to detect the presence of hemoglobin S; however, the SICKLEDEX™ test cannot distinguish the specific amount, concentration, or percentage of hemoglobin S in a sample. Moreover, SICKLEDEX™ cannot distinguish sickle cell anemia from sickle cell trait.

There has been a long-felt but unmet need for a sickle cell test that can provide point-of-care (POC), rapid, and accurate diagnosis of sickle cell disease. Furthermore, there is a need for a POC sickle cell test that can be easily operated by a user without medical expertise or training (a layperson). As will be clear from the disclosure that follows, the present invention provides solutions to address these needs.

SUMMARY

The present invention provides methods, kits, and medical devices (e.g., kits, cuvettes, and photometers) that can be used for an amount of hemoglobin S and/or total hemoglobin, and, optionally, expressing the amount of hemoglobin S as a percentage. For example the methods, kits and medical devices of the disclosure may be used for screening for sickle cell disease or sickle cell trait, distinguishing sickle cell zygosity, and/or quantifying the amount of hemoglobin-S in the blood of patients with sickle cell trait or disease (for example, by expressing the amount of hemoglobin-S as percentage of total hemoglobin).

The methods, kits, and medical devices of the disclosure may be used as point-of-care (POC) diagnostic methods, kits, and medical devices. Using the methods, kits, and devices of the disclosure an amount of hemoglobin S and/or total hemoglobin, and, optionally, a percentage of hemoglobin S can accurately be determined in seconds or minutes by a layperson using only microliters of a blood sample. Preferably, the blood sample is a undiluted whole blood sample collected directly from a patient at the point-of-care.

According to one aspect of the invention, a method for determining an amount of hemoglobin-S is provided. The method involves releasing an amount of total hemoglobin from red blood cells in a first volume of blood collected from a subject; mixing the amount of total hemoglobin, or an aliquot thereof, and a testing composition comprising an agent that selectively precipitates hemoglobin S to form a hemoglobin S precipitate in a mixture; measuring an optical absorbance of the hemoglobin S precipitate in the mixture, or an aliquot thereof, and translating the value of the optical absorbance into an amount of hemoglobin S. The aliquots mentioned above may be diluted or undiluted. In important embodiments, the blood is whole blood. In important embodiments, the whole blood is undiluted and is collected into a cuvette containing the reagents described below.

It was discovered, surprisingly, that there is a substantially linear relationship between the optical absorbance of the hemoglobin S precipitate formed according to the invention and the amount of hemoglobin S in whole blood, and that this phenomenon can be observed in undiluted whole blood despite the substantial turbidity created by the precipitate. It was known in the prior art that a precipitate formed, but measurement of optical absorbance was disregarded because of the substantial turbidity created by the precipitate. The precipitate formed a murky solution, so much so that it was not believed possible to obtain quantitative measurements. The inventors determined that there was a substantially linear relationship between optical absorbance and an amount of hemoglobin S in this murky solution and that amount (and, optionally, the percentage of hemoglobin S in the total hemoglobin) could be determined in whole blood using a point of care instrument. This invention permits determining the amount of hemoglobin S by drawing whole blood directly into a vessel such as, for example, a cuvette containing appropriate reagents, such as an anti-coagulant (e.g., EDTA), an agent for lysing red blood cells such as a detergent, an agent for selectively precipitating the Hemoglobin S and a buffer for maintaining a desirable pH. The optical measurement, preferably taken by a point of care, hand-held instrument, can then be translated by software in the instrument, which is preferably installed on a processor, encoding a first algorithm based upon a relationship between the value of the optical absorbance of the hemoglobin S precipitate and the amount of hemoglobin S. This relationship is shown in the data below.

In embodiments, the method can further involve: releasing an amount of total hemoglobin from red blood cells in a second volume of blood collected from the subject; mixing the amount of total hemoglobin and a control composition comprising an agent that converts hemoglobin into an optically detectable derivative of hemoglobin; measuring an optical absorbance of the optically detectable derivative, and translating the value of the optical absorbance of the optically detectable derivative into an amount of total hemoglobin. The translating can be performed by a second algorithm, preferably programmed into a second processor, and preferably in a point of care instrument, based upon a relationship between the value of the optically detectable derivative and the amount of total hemoglobin. The method of the invention also can involve translating the measurements of hemoglobin S and total hemoglobin into a percentage of hemoglobin S in the total hemoglobin. The translating can be performed by a third algorithm, preferably programmed into a third processor, and preferably in the point of care instrument, based upon a relationship between the amount of hemoglobin S measured in a volume of blood to the amount of total hemoglobin in a volume of blood from the same patient.

As will be understood by those of ordinary skill in the art, the absolute amount of hemoglobin S in a subject is very important to clinicians. Likewise, the amount of total hemoglobin in a subject is important to clinicians, as total hemoglobin can vary dramatically from patient to patient. As such, the relationship of hemoglobin S to total hemoglobin is an important measure to clinicians. The present invention permits a point of care determination of the patient's hemoglobin S, total hemoglobin, and the percentage of hemoglobin S in the total hemoglobin.

In any of the foregoing embodiments, the agent that forms a precipitate of hemoglobin S can be sodium hydrosulfate, sodium phosphate, sodium dithionite, sodium metabisulfite, or a hydrosulfate salt. In embodiments, the agent that selectively precipitates hemoglobin S is sodium hydrosulfate. Selectively precipitates hemoglobin S means hemoglobin S forms a precipitate but other forms of hemoglobin are not precipitated.

In any of the foregoing embodiments, the testing composition can include a buffering agent. Various buffering agents are described in detail below. Specific buffering agents are described in the examples.

It will be understood that measuring total hemoglobin in a volume can be performed by many methods well known in the art. A useful method for a point of care instrument involves creating a derivative of total hemoglobin and taking an optical measurement of the derivative. Such derivatives can be formed using cyanides or azides, for example.

In embodiments, the total hemoglobin can be mixed with an agent to convert the hemoglobin from a ferrous to a ferric state to form methemoglobin, which then combines with azide to form azidemethemoglobin. The optical absorbance of the azidemethemoglobin then can be made using the point of care instrument. Exemplary agents to convert the from a ferrous to a ferric state to form methemoglobin, include, but are not limited to, sodium nitrite and an azide. When measuring an optical absorbance of azidemethemoglobin, the methods and photometers of the disclosure may use a double wavelength measuring method, and, in preferred embodiments, measure an absorbance at each of 570 nm and 880 nm.

Alternatively, control compositions of the disclosure may comprise cyanide as an agent that binds tightly with the hemoglobin molecule to form cyanomethemoglobin. By measuring an optical absorbance of cyanomethemoglobin, preferably at a wavelength of 540 nanometers, the amount of total hemoglobin can be determined. Similar to the double wavelength measuring method that may be used for measuring an optical absorbance of azidemethemoglobin, when the control composition comprises cyanide that binds tightly with the hemoglobin molecule to form cyanomethemoglobin, the optical absorbance of cyanomethemoglobin may be measured at both 540 nm and 880 nm. The measurement of optical absorbance at 880 nm may be used to compensate for turbidity of the mixture.

According to one aspect of the invention, a method for monitoring an amount of hemoglobin-S is provided. The method involves determining a first amount of hemoglobin S, comprising releasing an amount of total hemoglobin from red blood cells in a first volume of blood collected from a subject; mixing the amount of total hemoglobin, or an aliquot thereof, and a testing composition comprising an agent that selectively precipitates hemoglobin S to form a hemoglobin S precipitate in a first mixture; measuring an optical absorbance of the hemoglobin S precipitate in the first mixture, or an aliquot thereof, and translating the value of the optical absorbance into a first amount of hemoglobin S; and determining a second amount of hemoglobin S, comprising releasing an amount of total hemoglobin from red blood cells in a second volume of blood collected from the subject; mixing the amount of total hemoglobin, or an aliquot thereof, and a testing composition comprising an agent that selectively precipitates hemoglobin S to form a hemoglobin S precipitate in a second mixture; measuring an optical absorbance of the hemoglobin S precipitate in the second mixture, or an aliquot thereof, and translating the value of the optical absorbance into a second amount of hemoglobin S wherein the first amount of hemoglobin S is determined before the second amount of hemoglobin S is determined, wherein an increase in the amount of hemoglobin S indicates, for example, an increase in severity of a sickle cell disease and/or complication in the subject, and wherein a decrease in the amount of hemoglobin S indicates, for example, a decrease in severity of a sickle cell disease and/or complication in the subject. In embodiments, the first and/or second amount of hemoglobin S may be determined during a period of time when the subject presents fewer and/or less severe symptoms of sickle cell disease or sickle cell trait. Alternatively, or in addition, in embodiments, the first and/or second amount of hemoglobin S may be determined during a period of time when the subject was asymptomatic. In embodiments, the first and/or second amount of hemoglobin S are determined at different times during the same medical procedure. Exemplary medical procedures include, but are not limited to, pre-natal care procedures to detect hemoglobin S amounts in a mother and/or a fetus, surgery, and blood transfusion. In a preferred embodiment of this method, the medical procedure is a blood transfusion. Furthermore, in embodiments, the first and/or second amounts of hemoglobin S are determined at different times during the same athletic or otherwise stressful event. Exemplary events include, but are not limited to, endurance exercise and/or activity involving low oxygen scenarios (e.g. high altitude or underwater diving situations).

In embodiments, the method for monitoring an amount of hemoglobin-S can involve translating the measurements of hemoglobin S and total hemoglobin into a percentage of hemoglobin S in the total hemoglobin. The translating can be performed by an algorithm, preferably programmed into a processor, and preferably in the point of care instrument, based upon a relationship between the amount of hemoglobin S measured in a volume of blood to the amount of total hemoglobin in a volume of blood from the same patient.

According to one aspect of the invention, a kit for determining an amount of hemoglobin-S and/or percentage of hemoglobin S in total hemoglobin is provided. The kit is a package containing a testing composition, a cuvette for obtaining a volume of red blood cells from a subject, and instructions for determining an amount of hemoglobin S according to the methods of the disclosure. In embodiments, the testing composition comprises an agent that selectively precipitates hemoglobin S to form a hemoglobin-S precipitate. In embodiments, the agent that selectively precipitates hemoglobin S does not precipitate hemoglobin A. Exemplary agents that selectively precipitates hemoglobin S include, but are not limited to, sodium hydrosulfate, sodium phosphate, sodium dithionite, sodium metabisulfite, and/or a hydrosulfate salt. In embodiments, the testing composition may include sodium hydrosulfate. In embodiments, the testing composition may further comprise a buffering agent. Moreover, in embodiments, the testing composition may further comprise a hemolysis agent.

In embodiments, a kit of the invention contains a testing composition, wherein the testing composition is provided in a cuvette. The testing composition may be provided as a liquid or in a liquid formulation. Alternatively, or in addition, the testing composition may be provided as a dry formulation. In certain aspects of this dry formulation, the dry formulation contacts an interior surface of the cuvette and mixes with a volume of red blood cells from a subject, preferably, but not necessarily, contained in whole blood. Either in a liquid or dry formulation, the testing composition may further comprise a buffering agent and/or a hemolysis agent.

Figure 1:
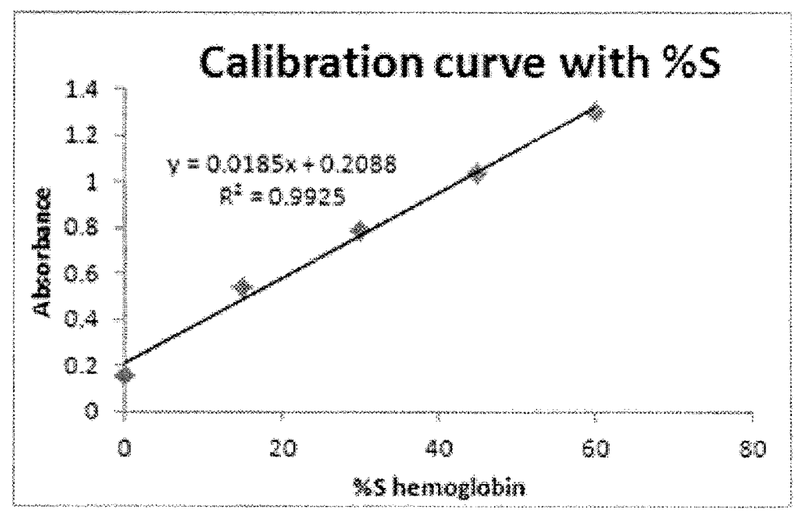
FIG. 1 is a graph showing that the point-of-care sickle cell testing system, including the methods, kits, and/or devices of the disclosure, can accurately quantify the percentage of hemoglobin-S in whole blood samples.

According to one aspect of the invention, a photometer for determining an amount of hemoglobin-S and/or the percentage of hemoglobin-S in total hemoglobin is provided. The photometer includes a first controller and a first processor, wherein an amount of hemoglobin S can be determined in a first volume of blood, wherein the first controller is configured to receive a measurement of optical absorbance, wherein the first processor is configured to translate the measurement of optical absorbance into an amount of hemoglobin S based on a first algorithm, and wherein the first processor outputs an amount of hemoglobin S to either a user interface or to a second controller. In embodiments, the first algorithm is based upon a relationship between the value of optical absorbance of a hemoglobin S precipitate and an amount of hemoglobin S. For example, the relationship between the value of optical absorbance of a hemoglobin S precipitate and an amount of hemoglobin S is determined by a preprogrammed data curve similar to the curve shown in FIG. 1. In embodiments, the device programmed to determine an amount of hemoglobin S, wherein an amount of total hemoglobin is released from red blood cells in the first volume of blood and mixed with an agent that specifically precipitates hemoglobin S to form a hemoglobin S precipitate in a first mixture, wherein the agent is sodium hydrosulfate. In an important embodiment, the volume of blood is a volume of whole blood. The first processor of this photometer may be an internal processor or internal microprocessor. Alternatively, first processor of this photometer may be an external processor or external microprocessor, including, but not limited to, a computer, laptop, tablet, or smart phone.

In another aspect of the invention, the photometer also can determine an amount of total hemoglobin. The photometer may determine an amount of total hemoglobin. A controller in the photometer is configured to receive a measurement of optical absorbance, a processor is configured to translate a measurement of optical absorbance into an amount of total hemoglobin based on an algorithm, and this processor outputs an amount of total hemoglobin to either a user interface or to a second controller. In embodiments, the second algorithm is based upon a relationship between the value of optical absorbance of an optically detectable derivative of hemoglobin and an amount of total hemoglobin. The relationship between the value of optical absorbance of an optically detectable derivative of hemoglobin and an amount of total hemoglobin may be determined by a preprogrammed data curve. In certain aspects of this photometer, the device is configured to detect and quantify azidemethemoglobin or cyanomethemoglobin. When using this photometer to determine an amount of total hemoglobin, the volume of blood optionally is a volume of anti-coagulated whole blood.

In certain embodiments of this photometer, the processors are an internal processor or internal microprocessor. Alternatively, the processors may be external processors or external microprocessors, including, but not limited to a computer, laptop, tablet, or smart phone.

Photometers of the invention, including a photometer programmed to determine an amount of hemoglobin S in a first volume of blood and to determine an amount of total hemoglobin in a second volume of blood, may expresses the amount of hemoglobin S as a percentage, wherein a second controller is configured to receive a first signal conveying an amount of hemoglobin S and a second signal conveying an amount of total hemoglobin, wherein a processor is configured to express the amount of hemoglobin S as a percentage based on an algorithm, and wherein this processor outputs a percentage of hemoglobin S to a user interface. The percentage may be calculated by dividing the amount of hemoglobin S by the amount of total hemoglobin and multiplying the dividend by 100. In embodiments, this processor may be an internal processor or internal microprocessor. Alternatively, this processor may be an external processor or external microprocessor, including, but not limited to a computer, laptop, tablet, or smart phone.

Processors of the disclosure may be components or programs contained a master processor. In embodiments, the master processor may be an internal processor or internal microprocessor. Alternatively, the master processor may be an external processor or external microprocessor, including, but not limited to a computer, laptop, tablet, or smart phone.

A first, second, or third processor of the disclosure may comprise a first, second, or third algorithm, respectively. Alternatively, first, second, or third processor of the disclosure may comprise any combination of a first, second, and/or third algorithm. Moreover, a master processor of the disclosure may comprise a first, second, and third algorithm. Processors of the disclosure may be internal or external to the photometers of the disclosure.

In preferred embodiments of the photometers of the disclosure, the photometer is a component of a HemoCue™ hemoglobin detection system. In certain aspects of the photometers of the disclosure, the kits and cuvettes of the disclosure may be used in conjunction with the photometers, generally, or in conjunction with a component of a HemoCue™ hemoglobin detection system specifically.

In embodiments of the methods and photometers of the disclosure, the photometer can perform spectrometry measurements at one or a plurality of wavelengths, including but not limited to, any wavelengths between 400 nm to 1200 nm, inclusive of the endpoints, or any wavelengths, including but not limited to between, 480 nm to 580 nm, 490 nm to 520 nm, 560 nm to 570 nm, 650 nm to 900 nm, 780 nm to 880 nm, 650 nm to 720 nm, and 750 nm to 800 nm, inclusive of the endpoints for each of these ranges. In certain embodiments of the methods, kits, and devices of the disclosure, the photometer uses a double wavelength measuring method for compensation of turbidity, wherein the first wavelength can be of any wavelength between 400 nm to 600 nm, inclusive of the endpoints, including but not limited to between, 480 nm to 580 nm, 490 nm to 520 nm, 520 nm to 560 nm, 550 nm to 570 nm, and 560 nm to 570 nm, inclusive of the endpoints for each range; wherein the second wavelength can be of any wavelength between 610 nm to 1300 nm, inclusive of the endpoints, including but not limited to between, 650 nm to 900 nm, 780 nm to 880 nm, 650 nm to 720 nm, 780 nm to 820 nm, and 750 nm to 800 nm, inclusive of the endpoints for each range.

To compensate for turbidity of a composition of the disclosure, methods, kits, and devices may further comprise a container for receiving a sample for background subtraction by a photometer.

In certain embodiments of the methods, kits, and devices of the disclosure, mixing a control composition comprising an agent that converts hemoglobin into an optically detectable derivative of hemoglobin with an amount of total hemoglobin released from red blood cells obtained from a volume of blood, induces a modified azidemethemoglobin reaction. For example, the erythrocyte membranes are disintegrated by sodium deoxycholate, releasing the hemoglobin. When the agent is sodium nitrite, the sodium nitrite converts the hemoglobin iron from the ferrous to the ferric state to form methemoglobin, which then combines with azide to form azidemethemoglobin. A photometer of the invention may use a double wavelength measuring method, preferably at wavelengths of 570 nm and 880 nm, for compensation of turbidity.

Alternatively, in certain embodiments of the methods, kits, and devices of the disclosure, mixing a control composition comprising an agent that converts hemoglobin into an optically detectable derivative of hemoglobin with an amount of total hemoglobin released from red blood cells obtained from a volume of blood, induces the formation of cyanomethemoglobin. When the agent contains cyanide, the cyanide binds tightly with the hemoglobin molecule to form cyanomethemoglobin. By measuring an optical absorbance of the cyanomethemoglobin, preferably at a wavelength of 540 nanometers, the amount of total hemoglobin can be determined. A photometer of the invention may use a double wavelength measuring method, preferably at wavelengths of 540 nm and 880 nm, for compensation of turbidity.

According to the methods, kits, and devices of the disclosure, a subject may carry zero (A/A), one (A/S) or two (S/S) copies of the sickle cell gene. A subject who does not carry any copy of the sickle cell gene (A/A) may be considered healthy and/or normal. Moreover, a subject who does not carry any copy of the sickle cell gene (A/A) may be considered asymptomatic because the subject does not present any sign or symptom of sickle cell disease or sickle cell trait. A subject who carries one copy of the sickle cell gene (A/S) may be considered asymptomatic, or asymptomatic over a period of time during which the subject presents no sign or symptom, a decreased number of signs or symptoms or a decreases severity of signs or symptoms of sickle cell disease or sickle cell trait. A subject to the disclosure who carries one or two copies of the sickle cell gene (A/S or S/S) may be considered symptomatic, or symptomatic over a period of time during which the subject presents a sign or symptom of sickle cell disease or sickle cell trait, a greater number of signs or symptoms of sickle cell disease or sickle cell trait, or a greater severity of a sign or symptom of sickle cell disease or sickle cell trait. For example, homozygous (S/S) subjects commonly exhibit symptoms of severe hemolytic anemia and/or vascular occlusion, which can lead to complications including chronic fatigue; chronic pain; infections; lung, liver and heart injury; leg ulcers; retinopathies; inflammation; arthritis; splenomegaly; and chronic lung infections. Although heterozygous (A/S) subjects may be asymptomatic, they may also develop severe complications, including early end stage renal failure, renal medullary carcinoma, and polycystic kidney diseases.

According to the methods, kits, and devices of the disclosure, total hemoglobin or an amount of total hemoglobin may comprise any form of hemoglobin, including, but not limited to hemoglobin A ($\alpha_2\beta_2$), hemoglobin A2 ($\alpha_2\delta_2$), hemoglobin F ($\alpha_2\gamma_2$), hemoglobin D-Punjab ($\alpha_2\beta^D_2$), hemoglobin H ($\beta_4$), hemoglobin Barts ($\gamma_4$), hemoglobin S ($\alpha_2\beta^S_2$), hemoglobin C ($\alpha_2\beta^C_2$), hemoglobin E ($\alpha_2\beta^E_2$). According to the methods, kits, and devices of the disclosure, total hemoglobin or an amount of total hemoglobin from a healthy or normal subject (a subject homozygous wild type A/A) may comprise hemoglobin A. According to the methods, kits, and devices of the disclosure, total hemoglobin or an amount of total hemoglobin from a subject carrying at least one copy of the sickle gene (a subject heterozygous for the sickle cell gene A/S or homozygous for the sickle cell gene S/S) may comprise hemoglobin A and hemoglobin S. Alternatively or in addition, according to the methods, kits, and devices of the disclosure, total hemoglobin or an amount of total hemoglobin from a subject carrying at least one copy of the sickle gene may comprise hemoglobin C and hemoglobin S. In certain aspects of the methods, kits, and devices of the disclosure, total hemoglobin or an amount of total hemoglobin may comprise hemoglobin A and hemoglobin S.

According to the methods, kits, and devices of the disclosure, an agent that selectively precipitates hemoglobin S precipitates only hemoglobin S. For example, an agent of the disclosure that selectively precipitates hemoglobin S does not also precipitate hemoglobin A ($\alpha_2\beta_2$), hemoglobin A2 ($\alpha_2\delta_2$), hemoglobin F ($\alpha_2\gamma_2$), hemoglobin D-Punjab ($\alpha_2\beta^D_2$), hemoglobin H ($\beta_4$), hemoglobin Barts ($\gamma_4$), hemoglobin S ($\alpha_2\beta^S_2$), hemoglobin C ($\alpha_2\beta^C_2$), and/or hemoglobin E ($\alpha_2\beta^E_2$). Agents of the disclosure that selectively precipitate hemoglobin S include reducing agents. Exemplary agents of the disclosure that selectively precipitate hemoglobin S include, but are not limited to sodium hydrosulfate, sodium phosphate, sodium dithionite, sodium metabisulfite, a hydrosulfate salt, and/or combinations thereof.

According to the methods, kits, and devices of the disclosure, a testing composition may comprise an agent that selectively precipitates hemoglobin S. Testing compositions of the disclosure may further comprise a buffering agent. Exemplary buffering agents of the disclosure include, but are not limited to a phosphate buffer solution, a sodium phosphate buffer solution, and/or a potassium phosphate buffering agent. Alternatively, or in addition, buffering agents of the disclosure may include, but are not limited to, acetate, sodium acetate, adipic acid, benzoic acid, sodium benzoate, citrate, malate, monobasic sodium phosphate, dibasic sodium phosphate, lactate, tartaric acid, potassium metaphosphate, potassium phosphate, monobasic sodium acetate, sodium bicarbonate, sodium tartrate, sodium citrate anhydrous and dehydrate, and/or combinations thereof. In certain embodiments of the methods, kits, and medical devices of the disclosure, the buffering agent comprises, consists essentially of, or consists of a phosphate buffer (such as potassium phosphate buffer and sodium phosphate buffer). In certain embodiments of the methods, kits, and medical devices of the disclosure, the buffering agent comprises, consists essentially of, or consists of a carbonate and/or bicarbonate buffer (such as, potassium carbonate buffer, sodium carbonate buffer, potassium bicarbonate buffer, and sodium bicarbonate buffer).

Buffering agents of the disclosure may be provided as a buffering solution having a molar concentration of between 0.1M to 5.0M, inclusive of the endpoints, or including but not limited to, molar concentrations of between 1.0M to 3.0M, inclusive of the endpoints, 1.5M to 2.5M, inclusive of the endpoints, and 2.0M to 2.3M, inclusive of the endpoints.

Buffering agents of the disclosure may be provided as a buffering solution having a pH of 6.5 to 9.5, or any pH values there between, including but not limited to, 6.9 to 8.5, 6.9 to 7.9, and 7.0 to 7.4, inclusive of the endpoints for each range. Moreover, buffering agents of the disclosure may be used to maintain the pH of a testing composition, at 6.5 to 9.5, or any pH values there between, including but not limited to, 6.9 to 8.5, 6.9 to 7.9, and 7.0 to 7.4., inclusive of the endpoints for each range. In certain embodiments of the method, kits, and devices of the disclosure, a buffering agent or buffering solution has a pH of 3.0 to 6.5, or any pH values there between, inclusive of the endpoints. In certain embodiments of the method, kits, and devices of the disclosure, a buffering agent or buffering solution may be used to maintain the pH of a testing composition, at 3.0 to 6.5, or any pH values there between, inclusive of the endpoints.

According to the methods, kits, and devices of the disclosure, a testing composition may comprise an agent that selectively precipitates hemoglobin S, a hemolysis agent, and, optionally, an anticoagulant. In certain embodiments of the methods, kits, and devices of the disclosure, a testing composition may comprise an agent that selectively precipitates hemoglobin S, a buffering agent, a hemolysis agent, and, optionally, an anticoagulant. Hemolysis agents of the disclosure are capable of disintegrating membranes of red blood cells and/or rupturing red blood cells. Exemplary hemolysis agents of the disclosure include, but are not limited to, a detergent, saponin; sodium deoxycholate; $NH_4Cl$ (ORTHO-MUNE); diethylene glycol (FACS LYSE); hypotonic agent (OPTILYSE B); ammonium chloride; ACK Lysing buffer A10492 (comprising ammonium chloride, potassium bicarbonate, and EDTA); and ERYTHROLYSE red blood cell lysing buffer. In certain embodiments of the methods, kits, and devices of the disclosure, hemolysis may also be achieved by freezing, sonication, and/or heating a volume of blood or red blood cells.

The subject matter of this application may involve, in some cases, interrelated products, alternative solutions to a particular problem, and/or a plurality of different uses of a single system or article.

Other advantages, features, and uses of the invention will become apparent from the following detailed description of non-limiting embodiments of the invention when considered in conjunction with the accompanying drawings In cases where the present specification and a document incorporated by reference include conflicting disclosure, the present specification shall control.

DETAILED DESCRIPTION

The present disclosure provides methods, kits, and devices (e.g. cuvettes and photometers) for use as point-of-care (POC) diagnostic systems for detecting, measuring, and quantifying hemoglobin-S; screening for sickle cell trait/disease; determining sickle cell zygosity; and quantifying an amount and/or percentage of hemoglobin-S. The methods, kits, and photometers of the disclosure may be used as POC diagnostic systems to determine an amount and/or percentage of hemoglobin-S in minutes by a layperson using only microliters of a blood or whole blood sample collected from a subject.

In certain embodiments of the methods, kits, and devices of the disclosure, a testing composition may be mixed with an amount of total hemoglobin released from a volume of red blood cells collected from a subject. In certain aspects of these embodiments, the testing composition may comprise an agent that selectively precipitates hemoglobin-S, a hemolysis agent, and a buffering agent. For example, a testing composition of the disclosure may include saponin as a hemolysis agent for lysing red blood cells, sodium hydrosulfite as a reducing agent for selectively precipitating hemoglobin-S, and potassium phosphate buffer as a buffering agent/solution. In certain embodiments of the methods, kits, and devices of the disclosure, an optical absorbance is determined using a photometer of the HemoCue™ hemoglobin system. For example, an agent that selectively precipitates hemoglobin-S is mixed with an amount of total hemoglobin released from a volume of red blood cells to form a hemoglobin S precipitate. In certain embodiments of the methods, kits, and devices of the disclosure, an optical absorbance of a hemoglobin S precipitate is determined using a photometer such as that of the HemoCue™ hemoglobin system.

In certain embodiments of the methods, kits, and devices of the disclosure, a composition may be used for determining an amount of total hemoglobin released red blood cells obtained in a volume of blood collected from a subject. Preferably, the blood is whole blood. Exemplary such compositions of the disclosure may comprise an agent that converts hemoglobin into an optically detectable derivative of hemoglobin. For example, the agent may convert the iron of hemoglobin from a ferrous to a ferric state to form methemoglobin, which then combines with azide to form azidemethemoglobin. An exemplary agent that converts the iron of hemoglobin from a ferrous to a ferric state to form methemoglobin is sodium nitrite. In certain embodiments of the composition, the composition comprises a hemolysis agent (such as sodium deoxycholate) capable of rupturing red blood cells, an agent (such as sodium nitrite) that converts hemoglobin iron from the ferrous to the ferric state to form methemoglobin, and/or an azide. By measuring an optical absorbance of cyanomethemoglobin, preferably at a wavelength of 570 nanometers, the amount of total hemoglobin can be determined. Alternatively, compositions of the disclosure comprise cyanide as an agent that binds tightly with the hemoglobin molecule to form the optically detectable derivative of hemoglobin, cyanomethemoglobin. By measuring an optical absorbance of cyanomethemoglobin, preferably at a wavelength of 540 nanometers, the amount of total hemoglobin can be determined. To compensate for turbidity in a mixture comprising an agent that converts hemoglobin into an optically detectable derivative of hemoglobin and an amount of hemoglobin released from red blood cells in a volume of blood obtained from a subject, an optical absorbance may also be measured at a wavelength of 880 nm in a double wavelength method of measurement.

Methods, kits, and devices of the disclosure may also contain a control sample or a series of control samples that may be assayed and/or compared to an amount of total hemoglobin or hemoglobin S released from red blood cells in a volume of blood obtained or collected from a subject. Each component of the methods, kits, and devices of the disclosure may be enclosed within an individual container. The entirety of containers of a method, kit, or device of the disclosure may be provided within a single package along with instructions for use.

In certain embodiments of the methods, kits, and devices of the disclosure, a testing composition may be applied to an amount of total hemoglobin released from red blood cells in a volume of blood obtained from a subject contained in a first cuvette and a control composition may be applied to an amount of total hemoglobin released from red blood cells in a volume of blood obtained from the same subject contained in a second cuvette. An optical absorbance may be determined for each of the first and second cuvettes either simultaneously or sequentially in a photometer. To provide a consistent basis of comparison, the volume of blood mixed with the testing composition and the volume of blood mixed with the control composition may be collected either simultaneously or sequentially from the same subject.

The disclosure provides methods, kits, and devices for determining an amount of hemoglobin S and/or an amount of total hemoglobin released from red blood cells in a volume of blood collected from a subject. An amount of hemoglobin S may be expressed in relative terms by comparing the amount of hemoglobin S to the volume of the blood (i.e. mass per volume), by comparing the amount of hemoglobin S to the volume of the mixture of testing composition and blood, or aliquot thereof (i.e. mass per volume), by comparing the amount of hemoglobin S to an amount of total hemoglobin (i.e. ratio or percentage of hemoglobin S), and/or by comparing a first amount of hemoglobin S to a second amount of hemoglobin S when the first and second amounts are measured at two distinct points in time (i.e. for monitoring hemoglobin S such as for tracking severity of a sickle cell disease or trait).

Devices (also referred to as medical devices) of the disclosure include, but are not limited to, a cuvette and a photometer.

Cuvettes of the disclosure include, for example, a capillary micro-cuvette. In certain embodiments of the methods, kits, and devices of the disclosure, the cuvette is disposable. Exemplary cuvettes for sampling a fluid via optical analyses may be found at U.S. Pat. Nos. 4,088,448, 5,674,457, and 5,064,282, each of which are herein incorporated by reference in their entirety.

Cuvettes of the disclosure may be substituted for other kinds of containers depending upon the type of device used to measure an optical absorbance of hemoglobin, including, but not limited to, test strips or test tubes to receive a red blood cells in a volume of blood. However, in certain embodiments of the disclosure, cuvettes provide a superior advantage when used to obtain or collect a volume of red blood cells and/or mix a composition of the disclosure with the volume of red blood cells. This superior advantage is present when the cuvettes of the disclosure are used in combination with a photometer, and preferably a photometer that is a component of a HemoCue™ hemoglobin detection system.

In certain embodiments, cuvettes (or alternative containers of the disclosure) may contain a volume of less than 500 µl, or any volume less than 500 µl, including but not limited to, less than 400 µl. less than 300 µl, less than 200 µl, less than 100 µl, less than 80 µl, less than 50 µl, less than 30 µl, less than 20 µl, less than 10 µl, less than 8 µl, less than 5 µl, less than 4 µl, less than 3 µl, less than 2 µl, or less than 1 µl.

Methods, kits, and devices of the disclosure may use a volume of blood of less than 500 µl, o any volume less than 500 µl, including but not limited to, a volume of less than 400 µl, less than 300 µl, less than 200 µl, less than 100 µl, less than 80 µl, less than 50 µl, less than 30 µl, less than 20 µl, less than 10 µl, less than 8 µl, less than 5 µl, less than 4 µl, less than 3 µl, less than 2 µl, less than 1 µl, less than 0.8 µl, less than 0.5 µl, less than 0.4 µl, less than 0.3 µl, less than 0.2 µl, less than 0.1 µl, less than 0.05 µl, less than 0.001 µl.

Cuvettes of the methods, kits, and devices of the disclosure may be formed from any suitable material, including but not limited to, transparent polymeric materials. In certain embodiments of the methods, kits, and devices of the disclosure, the cuvette is made of a material comprising or consisting of polystyrene.

Cuvettes of the disclosure may comprise a testing or control composition of the disclosure, either in a liquid or a dry formulation. When a testing and/or control composition of the methods, kits, or devices of the disclosure are provided as a dry formulation, the dry formulation may contact any part or the entirety of an interior surface of a cuvette of the disclosure. In certain aspects of these embodiments, the testing or control composition, when contained in a cuvette as either a liquid or a dry formulation mixes with a volume of blood collected from a subject. The volume of blood may be collected directly from the subject into a cuvette of the disclosure, and optionally, an amount of hemoglobin may be released from the volume of red blood cells upon entering for following entry into the cuvette. Lysis or rupture of red blood cells may be accomplished by physical means, including, but not limited to, dilution in an aqueous solution, freezing, centrifugation and sonication. Alternatively, or in addition, lysis or rupture of red blood cells may be accomplished by chemical means, including, but not limited to, inclusion of a hemolysis agent in a testing and/or control composition of the disclosure. When a cuvette comprises either a testing or control composition of the disclosure comprising a hemolysis agent, a volume of red blood cells may be ruptured or lysed leading to a release of total hemoglobin upon contact with the hemolysis agent, testing composition, and/or control composition. Preferred photometers of the disclosure are compatible with the cuvettes of the disclosure, and, conversely, preferred cuvettes of the disclosure are compatible with photometers of the disclosure. In certain embodiments, a preferred photometer is a photometer of the HemoCue™ hemoglobin detection system (see, U.S. Patent Publication No. 2009/0075324 and U.S. Pat. No. 5,064,282, each of which are hereby incorporated by reference in their entireties). Preferred photometers of the disclosure are hand-held devices intended for use at a point-of-care, and optionally, run off of battery power in the event that a source of power is not readily available.

According to the methods, kits, and devices of the disclosure, red blood cells may be collected, obtained, harvested, concentrated, or otherwise, isolated from a volume of blood collected or obtained from a subject. A blood sample of the disclosure may be, for example, unmodified whole blood collected directly from a subject, whole blood stored either with or without an anticoagulant, or otherwise modified whole blood. Whole blood samples that have been fractionated into one or more populations of red blood cells, plasma, serum, platelets, and/or white blood cells may be used in the methods, kits, or devices of the disclosure as long as the blood sample or fraction thereof contains red blood cells and/or an amount of total hemoglobin.

According to the methods, kits, and photometers of the disclosure, exemplary methods for determining an amount of total hemoglobin released from a volume of red blood cells include, but are not limited to, spectrophotometric and/or conductivity measurements. Measurement of an amount of total hemoglobin released from a volume of red blood cells based on conductivity has been described in Hirsch et al. (entitled The Relationship Between the Erythrocyte Concentration) and McMahon et al. (entitled The Specific Electro Conductivity of Blood), the contents of which are hereby each incorporated by reference in their entireties.

According to the methods, kits, and devices of the disclosure, an amount of hemoglobin S may be calculated based on the absorbance using the linear regression from the calibration curve: % S hemoglobin ("S %")=(Hemoglobin S concentration/total hemoglobin concentration)*100.

Subjects of the disclosure include human subjects. Human subjects may be selected from infants (less than 12 months of age), children (from 1 year to 14 years of age), and adults (aged 14 and above). Subjects of the disclosure (preferably human subjects) may have a family history of sickle cell trait/disease. Subjects of the disclosure (preferably human subjects) may belong to high-risk populations for sickle cell trait/diseases (including, but not limited to, descendants from Africa, South America, Central America (such as Panama), Caribbean islands, Mediterranean countries (such as Turkey, Greece, and Italy), India, and Saudi Arabia), and athletes (such as, high school, college, and professional athletes)). In certain embodiments of the disclosure, the subject has or is diagnosed with sickle cell disease (including sickle cell anemia and sickle cell trait).

Subjects of the disclosure further include any organism, including mammals such as primates, including apes, chimpanzees, orangutans, humans, and monkeys; and other animals such as dogs, cats, horses, cattle, pigs, sheep, goats, chickens, mice, rats, guinea pigs, and hamsters.

Testing compositions of the disclosure comprise an agent that precipitates hemoglobin S, and preferably, precipitates hemoglobin S, but does not precipitate other forms of hemoglobin, (e.g. hemoglobin A). Exemplary agents of the disclosure that specifically precipitate hemoglobin S include, but are not limited to, a reducing agent, sodium dithionite, sodium metabisulfite, and/or a hydrosulfite salt.

Testing and control compositions of the methods, kits, and devices of the disclosure may comprise a hemolytic agent that may disintegrate membranes of red blood cells and/or rupture red blood cells. Exemplary hemolytic agents of the disclosure, include, but are not limited to detergents, saponin; sodium deoxycholate; $NH_4Cl$ (ORTHO-MUNE); diethylene glycol (FACS LYSE); hypotonic agent (OPTIL-YSE B); ammonium chloride; ACK Lysing buffer A10492 (comprising ammonium chloride, potassium bicarbonate, and EDTA); and ERYTHROLYSE red blood cell lysing buffer. In certain embodiments of the methods, kits, and devices of the disclosure, hemolysis of red blood cells may achieved using freezing, centrifugation, sonication, dilution in an aqueous solution and/or heating.

Exemplary anticoagulants include calcium chelating agents such as EDTA and variants thereof and heparin.

Testing and control compositions of the methods, kits, and devices of the disclosure may comprise a buffering agent including, but not limited to, acetate, sodium acetate, adipic acid, benzoic acid, sodium benzoate, citrate, malate, monobasic sodium phosphate, dibasic sodium phosphate, lactate, tartaric acid, potassium metaphosphate, potassium phosphate, monobasic sodium acetate, sodium bicarbonate, sodium tartrate, sodium citrate anhydrous and dehydrate, and combinations thereof. In certain embodiments of the methods, kits, and devices of the disclosure, exemplary buffering agents may be solutions that comprise, consist essentially of, or consist of a phosphate buffer (such as potassium phosphate buffer and sodium phosphate buffer). In certain embodiments of the methods, kits, and devices of the disclosure, exemplary buffering agents may be solutions that comprise, consist essentially of, or consist of a carbonate and/or a bicarbonate buffer (such as, potassium carbonate buffer, sodium carbonate buffer, potassium bicarbonate buffer, and sodium bicarbonate buffer).

Buffering agents and solutions of the disclosure may have a molar concentration of 0.1M to 5.0M, inclusive of the endpoints, or any values there between, including but not limited to between, 1.0M to 3.0M, 1.5M to 2.5M, and 2.0M to 2.3M, inclusive of the endpoints for each range.

In certain embodiments of the methods, kits, and devices of the disclosure, a buffering agent or a buffer solution has a pH, or can be used to maintain the pH of one or more component of a testing and/or control composition, at 6.5 to 9.5, inclusive of the endpoints, or any pH values there between, including but not limited to between, 6.9 to 8.5, 6.9 to 7.9, and 7.0 to 7.4, inclusive of the endpoints for each range. In other embodiments, a buffering agent or buffering solution of the disclosure may have a pH, or can be used to maintain the pH of one or more components of a testing and/or control composition, at 3.0 to 6.5, inclusive of the endpoints, or any pH values there between.

Absorption measurements of the methods, kits, and devices of the disclosure may be performed by a processor using one or more algorithms for translating an optical absorbance to an amount of hemoglobin S and/or total hemoglobin or for expressing an amount of hemoglobin S as a percentage. In certain embodiments of the methods, kits, and devices of the disclosure, to determine an amount of total hemoglobin or hemoglobin S, spectrometry measurements may be made at one or a plurality of wavelengths, including, but not limited to, any wavelengths from between 400 nm to 1200 nm, inclusive of the endpoints, or any wavelengths there between, including but not limited to between, 480 nm to 580 nm, 490 nm to 520 nm, 560 nm to 570 nm, 650 nm to 900 nm, 780 nm to 880 nm, 650 nm to 720 nm, and 750 nm to 800 nm, inclusive of the endpoints for each range.

In certain embodiments of the methods, kits, and devices of the disclosure, a photometer may use a double wavelength measuring method for compensation of turbidity, wherein the first wavelength can be of any wavelength from between 400 nm to 600 nm, inclusive of the endpoints, including but not limited to between, 480 nm to 580 nm, 490 nm to 520 nm, 520 nm to 560 nm, 550 nm to 570 nm, and 560 nm to 570 nm, inclusive of the endpoints for each range; wherein the second wavelength can be of any wavelength from between 610 nm to 1300 nm, inclusive of the endpoints, including but not limited to between, 650 nm to 900 nm, 780 nm to 880 nm, 650 nm to 720 nm, 780 nm to 820 nm, and 750 nm to 800 nm, inclusive of the endpoints for each range. For example, in certain embodiments of the methods, kits, and devices of the disclosure, an optical measurement of an amount of hemoglobin-S, an amount of hemoglobin S precipitate, or an amount of total hemoglobin comprises: performing a first absorption measurement at a first wavelength of an amount of total hemoglobin or hemoglobin S in a first amount of hemoglobin released from a first volume of red blood cells and performing a second absorption measurement at a second wavelength, that is different from the first wavelength (at which the absorption is substantially different than at the first wavelength); and comparing the optical absorption measurements at each wavelength to determine an amount of total hemoglobin or hemoglobin S in an amount of hemoglobin released from red blood cells in a volume of blood obtained from a subject. In certain aspects of this embodiment, the second wavelength is smaller or substantially smaller than the first wavelength. Alternatively, in certain aspects of this embodiment, the second wavelength is larger or substantially larger than the first wavelength. To compensate for turbidity of a composition of the disclosure, methods, kits, and devices may further comprise a container for receiving a sample for background subtraction by a photometer. For example, the methods and photometers of the disclosure may measure an optical absorbance of a hemoglobin S precipitate or an optically detectable derivative of hemoglobin at a first wavelength of 570 nm (hemoglobin S precipitate), 570 nm (azidemethemoglobin) or 540 nm (cyanomethemoglobin) and a second wavelength of 880 nm. The optical absorbance measured at the first and second wavelengths may be averaged or subtracted from one another to compensate for turbidity.

According to the methods, kits, and devices of the disclosure, the term "absorption measurement," may refer to a measurement of optical absorption in an amount of total hemoglobin released from a volume of red blood cells collected from a subject. In an absorption measurement, the intensity of light detected after interacting with an amount of hemoglobin or hemoglobin precipitate or hemoglobin derivative is compared with the intensity of light irradiated from the amount of hemoglobin or hemoglobin precipitate or hemoglobin derivative. The detected light corresponds to the transmittance through the amount of hemoglobin or hemoglobin precipitate or hemoglobin derivative. The light that does not reach the detector is considered to have been absorbed by the amount of hemoglobin or hemoglobin precipitate or hemoglobin derivative. Thus, in the results of the measurements the transmittance may be used instead of the absorption. As the transmittance is the inverse of the absorption, detecting transmittance may be considered an absorption measurement. However, the measured absorption may not only correspond to light that has been truly absorbed in the amount of hemoglobin or hemoglobin precipitate or hemoglobin derivative, because some of the light may have been scattered in the amount of hemoglobin or hemoglobin precipitate or hemoglobin derivative so that some of the light does not reach the detector.

The methods, kits, and devices of the disclosure enable determination of an amount and/or a percentage of hemoglobin-S in less than 5 minutes or any time periods less than 5 minutes, including but not limited to, less than 4, minutes, less than 3 minutes, less than 2 minutes, less than 1 minute, less than 30 seconds, less than 15 seconds, less than 10 seconds, and less than 5 seconds.

The term "consisting essentially of," limits the scope of the reagents, devices, and steps to the specified materials or steps and those that do not materially affect the basic and novel characteristic(s) of the methods, kits, and devices of the disclosure. For instance, by using "consisting essentially of," the methods, kits, and devices of the disclosure do not contain a color chart, a filtering device, and/or a centrifuge. For instance, by using "consisting essentially of," the methods, kits, and devices of the disclosure do not comprise taking a visual color reading of a composition, filtering a composition, and/or centrifugation of a composition. Also, by using the term "consisting essentially of," methods, kits, and devices of the disclosure may comprise reagents (such as, carriers, preservatives), components (such as, boxes, instructions), and steps that do not materially affect the determination of an amount and/or a percentage of hemoglobin S in an amount of total hemoglobin released from a volume of red blood cells. Methods, kits, and devices of the disclosure do not comprise, or are not coupled to, a centrifuge. Methods, kits, and devices of the disclosure do not comprise a color chart or other means or instructions that instruct end users to take a visual reading of a composition of the disclosure. Methods, kits, and devices of the disclosure do not comprise performing electrophoresis, isolectric focusing, chromatography, antibody-based assay, genetic testing, or mass spectrometry.

Uses of the methods, kits, and devices of the disclosure include, but are not limited to, screening for sickle cell trait/disease in a subject (e.g., a fetus, a newborn, a baby, a child, an adult, or an aged individual); determining amount of hemoglobin-S in a subject belonging to a high-risk populations before pregnancy; screening for sickle cell trait and/or disease in athletes; screening for sickle cell trait and/or disease in a developing country and determining the amount of hemoglobin-S in a subject having been identified as carrying a sickle cell gene to monitor the treatment efficacy and/or progress (during a medical procedure, including, for example, a blood transfusion).

Methods, kits, and devices of the disclosure can operate under high temperatures (without the need for refrigeration), high humidity, and in a variety of altitudes. Methods, kits, and devices of the disclosure can be performed by a layperson.

EXAMPLES

Following is an example that illustrates embodiments and procedures for practicing the invention. The example should not be construed as limiting.

Example 1

Accurate and Rapid Determination of a Percentage of Hemoglobin-S

Methods, kits, and devices of the disclosure can be used to accurately determine the percentage of hemoglobin-S in whole blood samples.

For the following study, a testing composition comprising saponin, sodium hydrosulfite, and 2.3M potassium phosphate buffer solution; a microcuvette for receiving a whole blood sample; and a photometer (HemoCue™ Hemoglobin system) that determines the optical absorbance of the whole blood sample in the microcuvette were used. The photometer of the HemoCue™ Hemoglobin system uses a double wavelength measuring method, 570 nm and 880 nm, for compensation of turbidity. The reaction in the cuvette is a modified azidemethemoglobin reaction. The erythrocyte membranes are disintegrated by sodium deoxycholate, releasing the hemoglobin. Sodium nitrite converts the hemoglobin iron from the ferrous to the ferric state to form methemoglobin, which then combines with azide to form azidemethemoglobin. The photometer uses a double wavelength measuring method, 570 nm and 880 nm, for compensation of turbidity.

To determine the percentage of hemoglobin S, whole blood samples are obtained from sickle cell patients and normal subjects. A testing composition comprising sodium phosphate and potassium phosphate buffer solution, saponin, and sodium hydrosulfite is dispensed into a disposable micro-cuvette, and then 5 μl of the whole blood sample is added into the micro-cuvette. The microcuvette is then placed onto a micro-cuvette holder in the photometer (HemoCue™ Hemoglobin system). The percentage of hemoglobin-S in the whole blood sample is determined in 15 seconds.

Table 1 shows the percentage of hemoglobin-S determined by this study. The results are also presented in FIG. 1.

TABLE 1

| % Hb-S determined by POC system of the present invention | Absorbance (1st calculation) | Absorbance (2nd calculation) | Average |
|---|---|---|---|
| 60% | 1.301 | 1.298 | 1.2995 |
| 45% | 1.01 | 1.067 | 1.0385 |
| 30% | 0.765 | 0.813 | 0.789 |
| 15% | 0.532 | 0.541 | 0.5365 |
| 0% | 0.16 | 0.161 | 0.1605 |

Table 2 also shows measurements of the percentage of hemoglobin-S in whole blood samples.

TABLE 2

| Blood Sample # | Absorbance (1st calculation) | Absorbance (2nd calculation) | Average | % Hb-S determined by POC system of present invention | Actual % Hb-S |
|---|---|---|---|---|---|
| 1 | 1.084 | 1.117 | 1.1005 | 48% | 58% |
| 2 | L33 | 1.32 | 1.325 | 60% | 66% |
| 3 | 0.178 | 0.175 | 0.177 | 0% | 0% |
| 4 | 0.931 | 0.934 | 0.933 | 39% | 37% |
| 5 | 0.14 | 0.14 | 0.140 | 0% | 0% |

The methods of the disclosure can quantify %Hb-S using a few microliters of whole blood samples within a minute, and can be easily performed by a layman (such as a patient) who has no clinical training. For example, the point-of-care sickle cell testing system (including methods, kits, and devices of the disclosure) enables patients to determine the Hb-S% themselves at bed side at home before and after blood transfusions; this provides an easy way for patients to monitor the progress of sickle cell treatment.

Before the present invention, the percentage of hemoglobin-S was determined using electrophoresis, genetic testing, high-performance liquid chromatography (HPLC), isolectric focusing, antibody-based assay, or and mass spectrometry, all of which need to be conducted by health-care professionals and are time-consuming; as a result, when sickle cell crisis occurs in the middle of the night, it can be very difficult to promptly determine the percentage of Hb-S in order to provide life-saving treatment.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean " either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as " only one of "or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

REFERENCES

Hirsch F, Wood L, Ballard W C, Frey C, Wright I. The Relationship Between the Erythrocyte Concentration and the Specific Electro Conductivity of Blood. Bull NY Acad Med 1948; 24:393-4.

Luger T J1, Häussler R, Horvath T, Wagner C, Mutz N, Koller W. Determination of hemoglobin concentration using the hemoglobin azide method in traumatic emergencies. Anaesthesist 1990 June; 39(6):340.

McMahon D J, Carpenter R L. A comparison of conductivity-based hematocrit determinations with conventional laboratory methods in autologous blood transfusions. Anesth Analg 199071: 541-4.

Vanzetti, G. An azidemethemoglobin method for hemoglobin determination in blood. J. Lab. Clin. Med. 67, 116-26 (1966).

The invention claimed is:

1. A method for determining an amount of hemoglobin S, comprising:
   releasing an amount of total hemoglobin from red blood cells in a first volume of blood collected from a subject;
   mixing the amount of total hemoglobin, or an aliquot thereof, and a testing composition comprising an agent that selectively precipitates hemoglobin S to form a hemoglobin S precipitate in a mixture, the mixture being a solution;
   measuring an optical absorbance of the hemoglobin S precipitate in the mixture, or an aliquot thereof; and
   translating the value of the optical absorbance into an amount of hemoglobin S,
   wherein the translating is performed by a first algorithm based upon a relationship between the value of the optical absorbance of the hemoglobin S precipitate and the amount of hemoglobin S.

2. The method of claim 1, further comprising:
   releasing an amount of total hemoglobin from red blood cells in a second volume of blood collected from the subject;
   mixing the amount of total hemoglobin and a control composition comprising an agent that converts hemoglobin into an optically detectable derivative of hemoglobin;
   measuring an optical absorbance of the optically detectable derivative; and
   translating the value of the optical absorbance of the optically detectable derivative into an amount of total hemoglobin,
   wherein the translating is performed by a second algorithm based upon a relationship between the value of the optically detectable derivative and the amount of total hemoglobin.

3. The method of claim 2, further comprising a third algorithm which expresses the amount of hemoglobin S as a percentage of total hemoglobin.

4. The method of claim 1, wherein the amount of total hemoglobin comprises hemoglobin S and hemoglobin A.

5. The method of claim 1, wherein the agent that selectively precipitates hemoglobin S is sodium hydrosulfate, sodium phosphate, sodium dithionite, sodium metabisulfite, or a hydrosulfate salt.

6. A method for monitoring an amount of hemoglobin S, comprising:
   a) determining a first amount of hemoglobin S, comprising
   releasing an amount of total hemoglobin from red blood cells in a first volume of blood collected from a subject;
   mixing the amount of total hemoglobin, or an aliquot thereof, and a testing composition comprising an agent that selectively precipitates hemoglobin S to form a hemoglobin S precipitate in a first mixture, the first mixture being a solution;
   measuring an optical absorbance of the hemoglobin S precipitate in the first mixture, or an aliquot thereof; and
   translating the value of the optical absorbance into a first amount of hemoglobin S; and
   b) determining a second amount of hemoglobin S, comprising
   releasing an amount of total hemoglobin from red blood cells in a second volume of blood collected from the subject;
   mixing the amount of total hemoglobin, or an aliquot thereof, and a testing composition comprising an agent that selectively precipitates hemoglobin S to form a hemoglobin S precipitate in a second mixture, the second mixture being a solution;
   measuring an optical absorbance of the hemoglobin S precipitate in the second mixture, or an aliquot thereof; and
   translating the value of the optical absorbance into a second amount of hemoglobin S wherein the first amount of hemoglobin S is determined before the second amount of hemoglobin S is determined, wherein an increase in the amount of hemoglobin S indicates an increase in severity of a sickle cell disease and/or complication in the subject, and wherein a decrease in the amount of hemoglobin S indicates a decrease in severity of a sickle cell disease and/or complication in the subject.

* * * * *

UNITED STATES PATENT AND TRADEMARK OFFICE
CERTIFICATE OF CORRECTION

PATENT NO. : 9,995,757 B2
APPLICATION NO. : 14/917741
DATED : June 12, 2018
INVENTOR(S) : Mark J. Rice et al.

It is certified that error appears in the above-identified patent and that said Letters Patent is hereby corrected as shown below:

On the Title Page

In the Inventors section, Item (72), the second named inventor, "Lindsay Bazydlo, Gainesville, FL (US)" should read --Lindsay Bazydlo, Charlottesville, VA (US)--

Signed and Sealed this
Twenty-first Day of August, 2018

Andrei Iancu
*Director of the United States Patent and Trademark Office*